US00PP31304P2

(12) United States Plant Patent
Pineau

(10) Patent No.: US PP31,304 P2
(45) Date of Patent: Dec. 31, 2019

(54) ***HIBISCUS* 'MINSYPIN3'**

(50) Latin Name: *Hibiscus syriacus*
Varietal Denomination: MINSYPIN3

(71) Applicant: Patrick Pineau, Saint Mathurin sur Loire (FR)

(72) Inventor: Patrick Pineau, Saint Mathurin sur Loire (FR)

(73) Assignee: Hortival Diffusion SAS (FR)

( * ) Notice: Subject to any disclaimer, the term of this patent is extended or adjusted under 35 U.S.C. 154(b) by 0 days.

(21) Appl. No.: 16/350,724

(22) Filed: Dec. 20, 2018

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ..... A01H 5/02; A01H 6/60
See application file for complete search history.

*Primary Examiner* — Annette H Para
(74) *Attorney, Agent, or Firm* — Cassandra Bright

(57) ABSTRACT

A new and distinct *Hibiscus* cultivar named 'MINSYPIN3' is disclosed, characterized by large, single, pink flowers with a darker eye, up to 12 cm in diameter. Plants are well-branched, upright and vigorous. The new variety is a *Hibiscus*, normally produced as an outdoor garden or container plant.

3 Drawing Sheets

Figure 1:
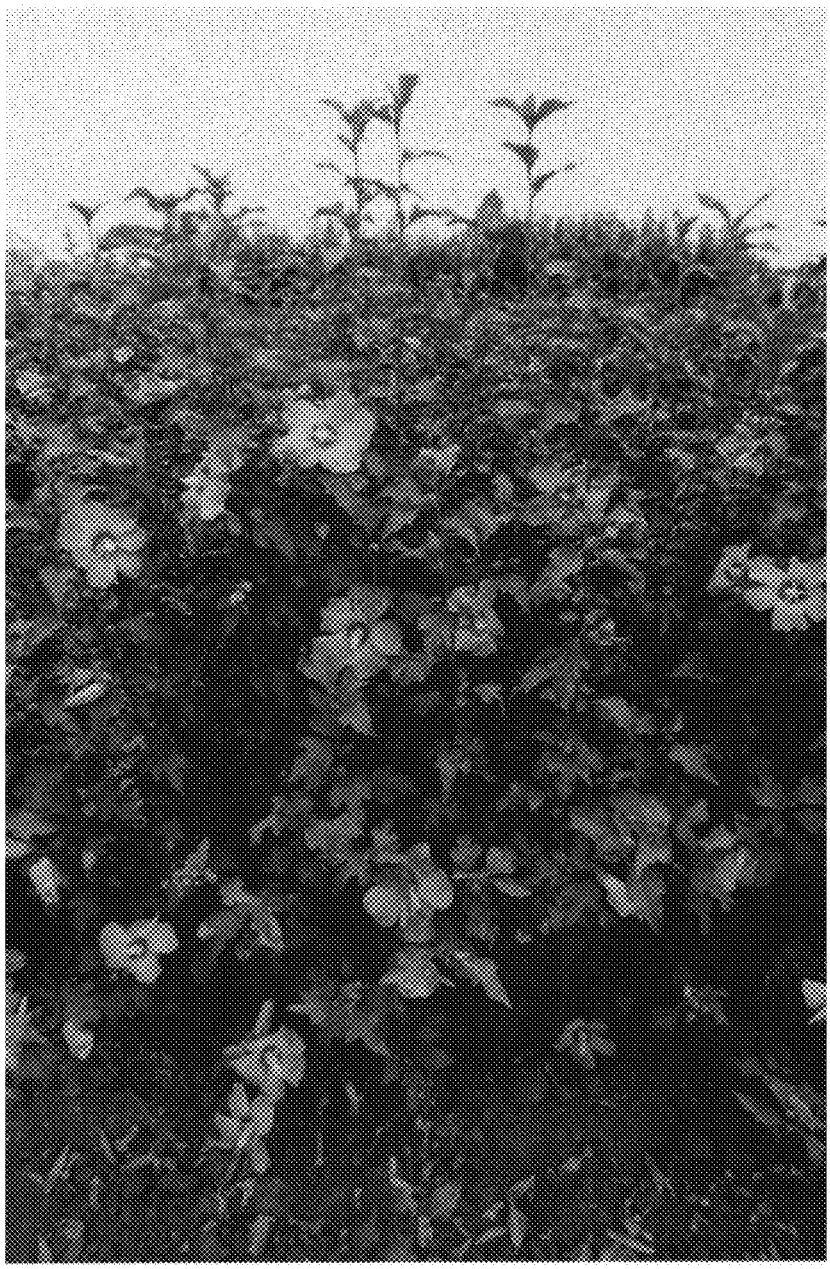

Latin name of the genus and species: *Hibiscus syriacus*. Variety denomination: 'MINSYPIN3'.

BACKGROUND OF THE INVENTION

The new *Hibiscus* cultivar is a product of a planned breeding program conducted by the inventor, Patrick Pineau. The objective of the breeding program was to look for a new *Hibiscus syriacus* cultivars with large flowers and healthy, vigorous foliage. The cross resulting in this new variety was made during 2004.

The seed parent is the unpatented, proprietary *Hibiscus syriacus* 'R3-08'. The pollen parent is the unpatented variety *Hibiscus syriacus* 'Red Heart'. The new variety was identified and selected as a potentially interesting selection in October 2007. Selection was made at a nursery in La Menitre, France.

Asexual reproduction of the new cultivar 'MINSYPIN3' was first performed in January 2008 in La Menitre, France, by grafting. Subsequent propagation has shown that the unique features of this cultivar are stable and reproduced true to type in 6 successive generations.

SUMMARY OF THE INVENTION

The cultivar 'MINSYPIN3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINSYPIN3' These characteristics in combination distinguish 'MINSYPIN3' as a new and distinct *Hibiscus* cultivar:

1. Large pink single flower with a red eye.
2. Erect plant form.
3. Well branched.
4. Vigorous.

PARENT COMPARISON

Plants of the new cultivar 'MINSYPIN3' are similar to plants of the seed parent variety in most horticultural characteristics, however, plants of the new cultivar 'MINSYPIN3' differ in the following;

1. The new variety has more branches than the seed parent.
2. The new variety has a dark eye, the seed parent does not.

Plants of the new cultivar 'MINSYPIN3' are similar to plants of the pollen parent variety *Hibiscus syriacus*, 'Red Heart' in most horticultural characteristics, however, plants of the new cultivar 'MINSYPIN3' differ in the following;

1. 'Minsypin3' is more vigorous with more branches than the pollen parent.
2. 'Minsypin3' has a pink flower with a dark eye, the pollen parent has a white flower.
3. 'Minsypin3' has a larger flower (12 cm) than the pollen parent (8-10 cm).
4. 'Minsypin3' has small pink petaloid stamens, the pollen parent has none.
5. 'Minsypin3' has got longer red feathering (0.5 to 1 cm) which is absent in the pollen parent.
6. 'Minsypin3' has shorter pubescence on its seed than the pollen parent.

COMMERCIAL COMPARISON

Plants of the new cultivar 'MINSYPIN3' can be compared to the variety *Hibiscus syriacus* unpatented. These varieties are similar in most horticultural characteristics however, 'MINSYPIN3' differs in the following:

1. 'Minsypin3' is more erect than 'Flogi'.
2. 'Minsypin3' has a larger flower (12 cm) than 'Flogi' (10 cm).

3. 'Minsypin3' has lighter pink petals color than 'Flogi'.
4. 'Minsypin3' has small pink petaloid stamens 'Flogi', has none.
5. 'Minsypin3' has got longer red feathering (0.5 to 1 cm) than 'Flogi' (0.5 cm).
6. 'Minsypin3' produces more seed than 'Flogi'.

BRIEF DESCRIPTION OF THE PHOTOGRAPHS

The accompanying photograph in FIG. 1 illustrates in full color a typical plant of 'MINSYPIN3' grown in the ground at approximately 10 years old in La Menitre, France.

Figure 2:
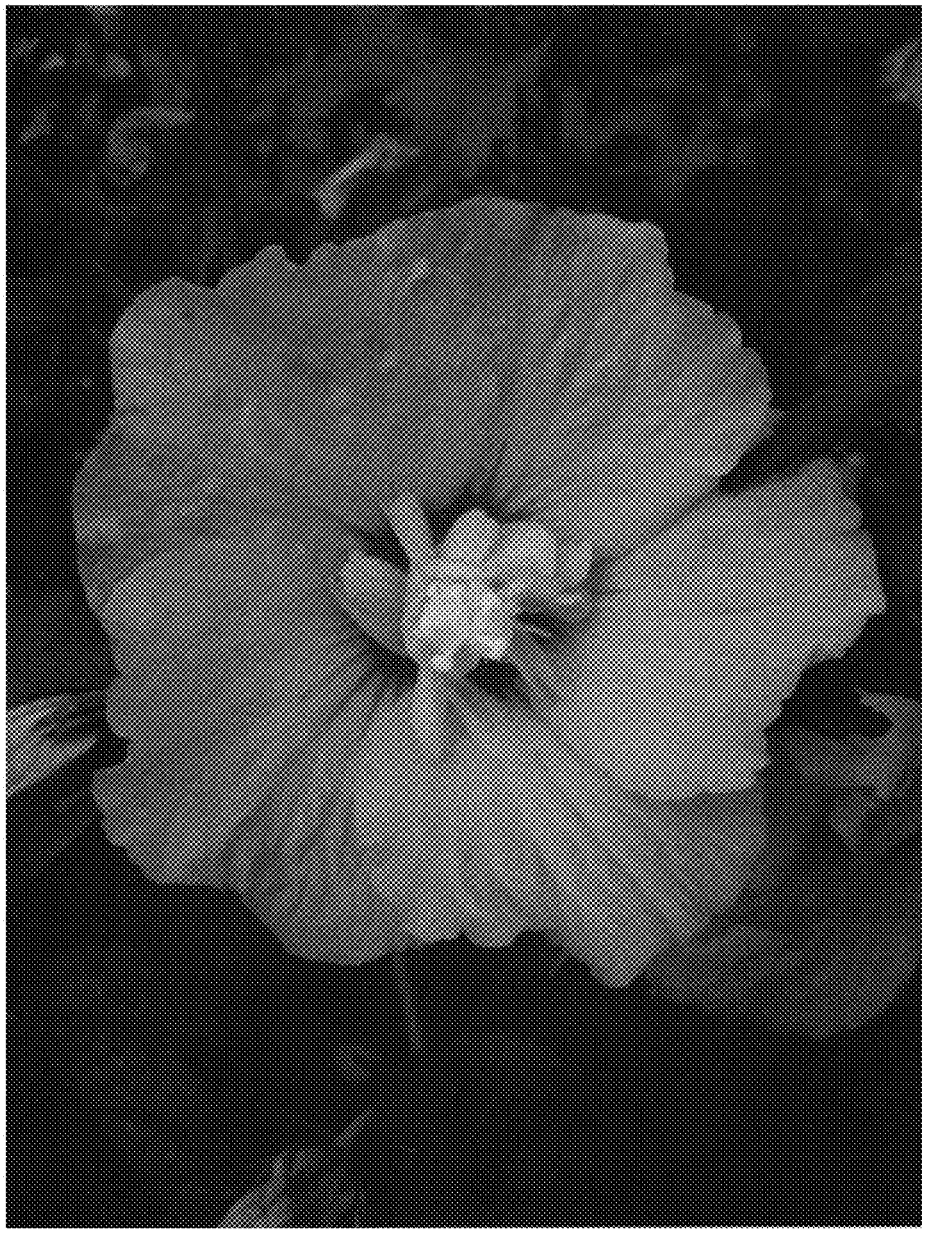

FIG. 2 illustrates in full color a typical flower of 'MINSYPIN3'.

Figure 3:
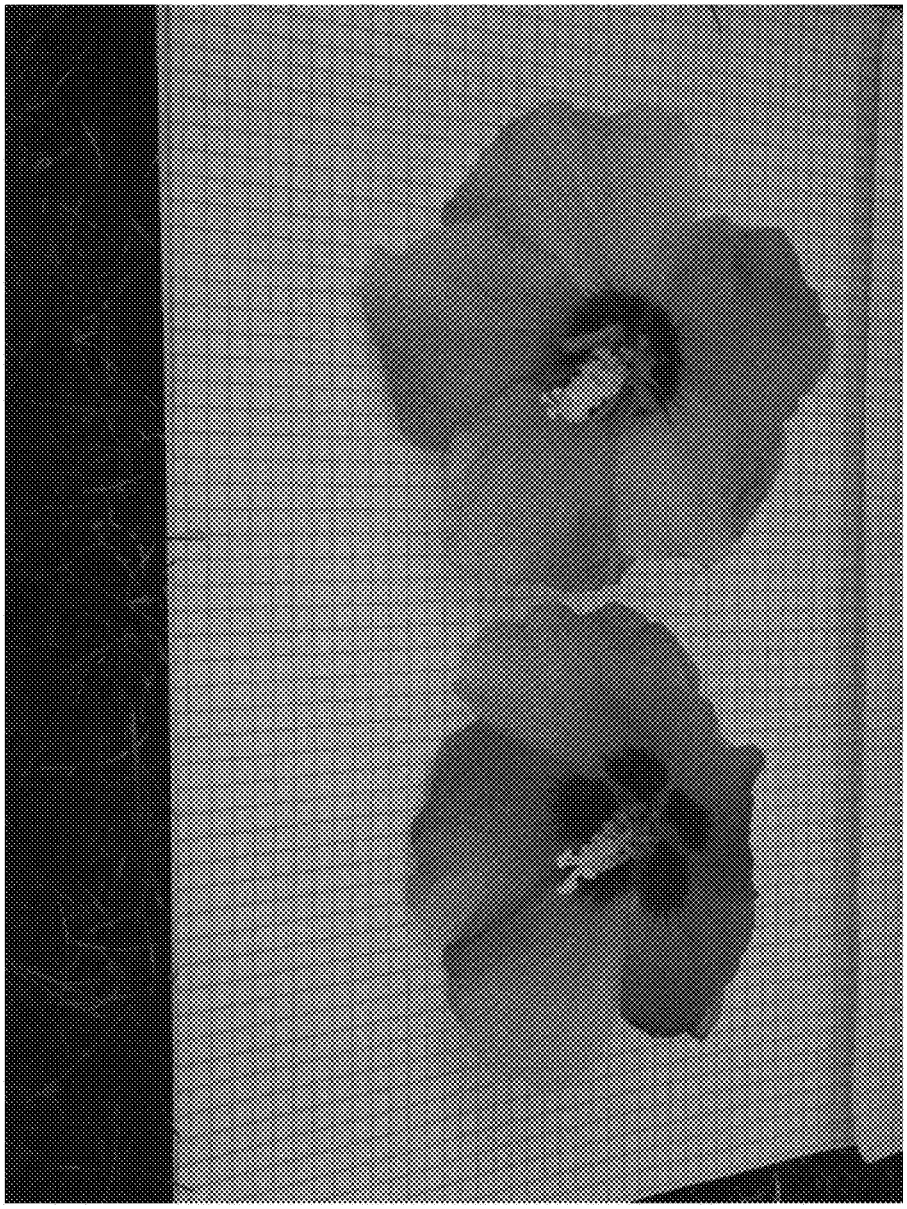

FIG. 3 compares a flower of 'Minsypin3', on the top of the figure, to a flower of 'Flogi', on the bottom of the photo.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'MINSYPIN3' plants grown in an unheated polyhouse in La Menitre, France, under natural lighting. Measurements were taken during September of 2018. The plants were 10 years old and planted in the ground. The growing temperature ranged from approximately −5° C. to 27° C. Measurements and numerical values represent averages of typical plant types.

Botanical classification: *Hibiscus syriacus* 'MINSYPIN3'.

PROPAGATION

Time to initiate roots: 20 days at approximately 25° C.

Root description: Fibrous, medium root thickness. Tan/brown in color, not effectively measured with a color chart.

Time to produce a rooted young plant: About 90 days at 25° C.

PLANT

Plant type: Perennial, hardy deciduous flowering shrub.

Age of plant described: Approximately 10 years old.

Growth habit: Erect, vigorous.

Height: 120 cm.

Branching characteristics: Well branched.

Length of primary lateral branches: 90 cm.

Quantity of lateral branches: 8.

Characteristics of primary lateral branches:

*Diameter.*—0.4 cm.

*Color.*—RHS Yellow-Green 147C.

Internode length: 6 cm.

FOLIAGE

Leaf:

*Arrangement.*—Alternate.

*Quantity.*—Approximately 25 per branch.

*Average Length.*—10 cm.

*Average Width.*—4.5 cm.

*Shape of blade.*—Ovate, lobed. Shallow to moderately lobed, 3 to 5 lobes.

*Apex.*—Acute.

*Base.*—Obtuse.

*Margin.*—Few irregular serrations on a mainly, entire, lobed margin.

*Texture of top surface.*—Glabrous.

*Texture of bottom surface.*—Rough, with sparse adpressed hairs along veins.

*Color.*—Young foliage upper side: RHS Green 137B. Young foliage under side: RHS Green 137B. Mature foliage upper side: RHS Green 137A. Mature foliage under side: RHS Green 137B.

*Fall or Winter coloration variance.*—None.

*Venation.*—Type: Pinnate. Venation color upper side: RHS Green 137D. Venation color under side: RHS Green 143C.

*Petiole.*—Length: 2.5 cm. Diameter: 0.15 cm. Color: RHS Yellow-Green 144A.

FLOWER

Natural flowering season: July to September.

Flower type and habit: Solitary, rotate.

*Single, double, multiplex.*—Single.

*Petals overlapping.*—Moderately overlapping.

Rate of flower opening: 1 to 2 days from bud to fully opened flower.

Flower longevity on Plant: 1 to 2 days.

Persistent or self-cleaning: Self-cleaning.

Bud:

*Shape.*—Ovate.

*Length.*—3.1 cm.

*Diameter.*—1.3 cm.

*Color.*—RHS Red-Purple 59B.

Flower size:

*Diameter.*—12 cm.

*Depth.*—3 cm.

Petals:

*Quantity.*—5.

*Arrangement.*—Rotate.

*Length.*—6 cm.

*Width.*—4 cm.

*Shape.*—Broad rounded deltoid.

*Apex.*—Rounded.

*Base.*—Obovate.

*Margin.*—Entire.

*Texture, upper and lower surfaces.*—Glabrous.

*Color.*—When opening, upper surface: RHS Red-Purple N74D, blushed with Red-Purple 71A. When opening, lower surface: RHS Red-Purple N74D, blushed with Red-Purple 71C. Fully opened, upper surface: RHS Red-Purple N74D, blushed with Red-Purple 71B. Fully opened, lower surface: RHS Red-Purple N74D, blushed with Red-Purple 71C. Color basal blotch: RHS Red-Purple 59A. Ratio of basal blotch/petal size: About 25% of petal blade blotched. Feathering color: RHS Red-Purple 59A. Feathering size(length): 0.8 cm.

Petaloids:

*Arrangement.*—Small central whorl of stamenal petaloids at the base of the style and along the style.

*Number of petaloids per flower.*—Average range 10 to 20.

*Shape.*—Oblanceolate.

*Base.*—Truncate.
*Margin.*—Entire.
*Tip shape.*—Obtuse, irregular very shallow lobes.
*Length.*—1 to 2.5 cm.
*Width.*—6 to 15 mm.
*Texture.*—Upper: Glabrous. Lower: Glabrous.

Petaloid color:
*When opening, upper surface.*—RHS Red-Purple N74D. When opening, lower surface: RHS Red-Purple N74D. Fully opened, upper surface: RHS Red-Purple N74D. Fully opened, lower surface: RHS Red-Purple N74D.

Sepals:
*Quantity.*—5.
*Length.*—2 cm.
*Width.*—0.7 cm.
*Shape.*—Ovate.
*Margin.*—Entire.
*Color.*—RHS Green 144B.

Peduncles:
*Length.*—2 cm.
*Diameter.*—0.3 cm.
*Angle.*—About 45° to the lateral branch.
*Strength.*—Strong.
*Texture.*—Glabrous.
*Color.*—RHS Green 144B.

Fragrance: None.

REPRODUCTIVE ORGANS

Stamens:
*Number.*—50.

Anthers:
*Shape.*—Irregular sphere.
*Length.*—0.3 cm.
*Color.*—Near RHS yellow-White 158C.
*Pollen color.*—RHS Yellow 4D.
*Pollen amount.*—Abundant.

Pistil:
*Number.*—1.
*Length.*—3.5 cm.
*Style.*—Length: 3 cm. Color: Near RHS White 155C.
*Stigma.*—Shape: Rounded disc. Color: Near RHS White 155C.
*Ovary color.*—Near RHS Yellow-Green 145C.

OTHER CHARACTERISTICS

Seeds and fruits: Capsule, typically about 1 cm in diameter and length. Pubescent, colored near Grey-Brown 199B. Abundant pubescent seed.

Disease/pest resistance: Neither resistance nor susceptibility to normal diseases and pests of *Hibiscus syriacus* have been observed.

Temperature tolerance: Low temperature tolerance to at least USDA zone 4, high temperature tolerance to at least 40° C.

What is claimed is:

1. A new and distinct cultivar of *Hibiscus* plant named 'MINSYPIN3' as herein illustrated and described.

* * * * *